United States Patent
Flagle et al.

(10) Patent No.: US 7,442,206 B2
(45) Date of Patent: Oct. 28, 2008

(54) METHODS AND SYSTEMS FOR MODIFYING VASCULAR VALVES

(75) Inventors: Jacob A. Flagle, Indianapolis, IN (US); Brian C. Case, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 418 days.

(21) Appl. No.: 11/260,360

(22) Filed: Oct. 27, 2005

(65) Prior Publication Data
US 2006/0136045 A1  Jun. 22, 2006

Related U.S. Application Data

(60) Provisional application No. 60/622,765, filed on Oct. 28, 2004.

(51) Int. Cl.
*A61F 2/24* (2006.01)
(52) U.S. Cl. .................. 623/2.1; 623/904; 623/1.24; 606/142
(58) Field of Classification Search ................ 623/1.24, 623/2.1, 904; 606/142
See application file for complete search history.

(56) References Cited

U.S. PATENT DOCUMENTS

| | | | |
|---|---|---|---|
| 4,218,782 A | 8/1980 | Rygg | |
| 4,902,508 A | 2/1990 | Badylak et al. | |
| 4,956,178 A | 9/1990 | Badylak et al. | |
| 5,275,826 A | 1/1994 | Badylak et al. | |
| 5,281,422 A | 1/1994 | Badylak et al. | |
| 5,411,552 A | 5/1995 | Andersen et al. | |
| 5,516,533 A | 5/1996 | Badylak et al. | |
| 5,554,389 A | 9/1996 | Badylak et al. | |
| 5,584,861 A | 12/1996 | Swain et al. | |
| 5,609,598 A | 3/1997 | Laufer et al. | |
| 5,810,847 A * | 9/1998 | Laufer et al. | 606/142 |
| 5,855,601 A | 1/1999 | Bessler et al. | |
| 5,955,110 A | 9/1999 | Patel et al. | |
| 5,993,844 A | 11/1999 | Abraham et al. | |
| 6,036,687 A | 3/2000 | Laufer et al. | |
| 6,099,567 A | 8/2000 | Badylak et al. | |
| 6,126,686 A * | 10/2000 | Badylak et al. | 623/1.24 |
| 6,149,660 A | 11/2000 | Laufer et al. | |
| 6,165,183 A | 12/2000 | Kuehn et al. | |
| 6,200,336 B1 | 3/2001 | Badylak et al. | |
| 6,206,931 B1 | 3/2001 | Cook et al. | |
| 6,444,229 B2 | 9/2002 | Voytik-Harbin et al. | |
| 6,475,232 B1 | 11/2002 | Babbs et al. | |
| 6,508,833 B2 | 1/2003 | Pavcnik et al. | |
| 6,575,971 B2 | 6/2003 | Hauck et al. | |
| 6,695,866 B1 | 2/2004 | Kuehn et al. | |

(Continued)

FOREIGN PATENT DOCUMENTS

EP   0 442 588   8/1991

(Continued)

*Primary Examiner*—Suzette J Gherbi
(74) *Attorney, Agent, or Firm*—Woodard, Emhardt, Moriarty, McNett & Henry LLP

(57) ABSTRACT

Described are methods and systems for modifying vascular valves in order to reduce retrograde blood flow through the valves. Preferred methods include connecting vascular valve leaflets with at least one remodelable material, such that the valve leaflets become fused by the ingrowth of the patient's native tissue. Preferred remodelable materials include collagenous extracellular matrix material, such as small intestine submucosa.

26 Claims, 5 Drawing Sheets

U.S. PATENT DOCUMENTS

| | | |
|---|---|---|
| 6,716,241 B2 | 4/2004 | Wilder et al. |
| 6,752,813 B2 | 6/2004 | Goldfarb et al. |
| 6,752,828 B2 | 6/2004 | Thornton |
| 2002/0010418 A1 | 1/2002 | Lary et al. |
| 2003/0093071 A1 | 5/2003 | Hauck et al. |
| 2004/0167539 A1 | 8/2004 | Kuehn et al. |
| 2005/0149069 A1 * | 7/2005 | Bertolero et al. ............ 606/151 |

FOREIGN PATENT DOCUMENTS

| | | |
|---|---|---|
| GB | 2 165 559 | 8/1986 |
| WO | WO 96/20655 | 7/1996 |
| WO | WO 2004/089253 | 10/2004 |
| WO | WO 2005/020847 | 3/2005 |

* cited by examiner

METHODS AND SYSTEMS FOR MODIFYING VASCULAR VALVES

STATEMENT OF RELATED APPLICATIONS

This application claims the benefit of priority of U.S. Provisional Patent Application Ser. No. 60/622,765 filed Oct. 28, 2004 which is incorporated herein by reference in its entirety.

BACKGROUND

The present invention relates generally to a method for modifying vascular valves. One aspect of the present invention provides a method for modifying the leaflets of one or more venous valves with an extracellular matrix (ECM) material in order to enhance the valve or valves.

As further background, vascular vessels are comprised of tissue and are the conduit for circulating blood through a mammalian body. A vascular vessel that carries blood from the heart is known as an artery. A vascular vessel that returns blood to the heart is known as a vein. There are three types of veins in a human: deep veins, which are located deep in the body close to the bones, superficial veins, which are located close to the skin, and perforating veins, which are smaller veins that connect the deep veins to the superficial veins.

To assist blood flow, venous vascular vessels contain venous valves. Each venous valve is located inside the vein and typically includes at least two valve leaflets, which are disposed annularly along the inside wall of the vein. These leaflets open to permit blood flow toward the heart and close, upon a change in pressure, to restrict the back flow of blood. When blood flows towards the heart, the venous pressure forces the valve leaflets to move apart in a downstream flexing motion, thereby creating an open path for blood flow. The leaflets normally flex together when moving in the upstream direction; therefore, they return to a closed position to restrict or prevent blood flow in the upstream, or retrograde, direction after the venous pressure is relieved. The leaflets, when functioning properly, extend radially inward toward one another such that the leaflet tips, or cusps contact each other when the valve is closed.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood will collect, or pool in vessels below the valve. This pooling of blood causes an increase in the venous pressure beneath the valve. Venous valves that allow such deleterious retrograde flow are known as incompetent or inadequate venous valves. The condition resulting from such incompetent venous valves is known as venous valve insufficiency.

In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

A common method of treatment for venous valve insufficiency is the placement of an elastic stocking around the patient's leg to apply external pressure to the vein, forcing the walls radially inward to force the leaflets into apposition. Although sometimes successful, the tight stocking is quite uncomfortable, especially in warm weather, because the stocking must be constantly worn to keep the leaflets in apposition. The elastic stocking also affects the patient's physical appearance, thereby potentially having an adverse psychological affect. This physical and/or psychological discomfort can lead to the patient removing the stocking, thereby inhibiting treatment.

Surgical methods for treatment of venous valve insufficiency have also been developed. A vein with incompetent venous valves can be surgically constricted to bring incompetent leaflets into closer proximity in hopes of restoring natural valve function. Methods for surgical constriction of an incompetent vein include implanting a frame around the outside of the vessel, placing a constricting suture around the vessel (e.g., valvuloplasty), or other types of treatment to the outside of the vessel to induce vessel contraction. Other surgical venous valve insufficiency treatment methods include bypassing or replacing damaged venous valves with autologous sections of veins containing competent valves.

Another surgical method includes vein stripping and ligation. In this procedure, the femoral vein and other major venous tributaries are disconnected from the greater saphenous vein and tied off. Next, the greater saphenous vein is removed from the leg by advancing a wire through the vein, tying the wire to a saphenous vein end, and then pulling the wire, and vein, out through an incision in the upper calf or ankle. Unfortunately, the above surgeries require at least one incision, and have several undesirable side effects and risks, such as a long patient recovery time, the potential for scarring, and numerous other risks inherent with surgery, such as those associated with administration of anesthesia.

Recently, various implantable prosthetic devices and minimally invasive methods for implantation of these devices have been suggested to treat venous valve insufficiency. Such prosthetic devices can be inserted intravascularly, for example from an implantation catheter. Prosthetic devices can function as a replacement venous valve, or enhance venous valve function by bringing incompetent valve leaflets into closer proximity. In one procedure, venous valve function can be enhanced by clipping the valve leaflets together with a clip made from a biocompatible material, such as a metal, polymer, or fabric. In other procedures, venous valve leaflets can be attached using a plastic or metal staple.

Recently, a number of methods have been suggested to treat varicose veins and venous valve leaflets with energy sources, such as radiofrequency (RF) energy. In one such method, valve leaflets can be fastened together with electrodes delivering RF energy. In another such method, a catheter having an electrode tip can be used to apply RF energy to cause localized heating and corresponding shrinkage of venous tissue. After treatment of one venous section is complete, the catheter can be repositioned to treat a different venous section.

Methods for treatment of varicose veins have also been developed involving various forms of sclerotherapy. Generally, sclerotherapy involves the delivery of one or more sclerosing agents to the lumen of a vein, which induce the vein to collapse and the venous walls to fuse, thereby closing the vein.

In view of the above background, the need remains for improved and alternative methods and systems for affecting the venous system to treat venous conditions. The present invention is addressed to these needs.

SUMMARY

In one aspect, the invention relates to surgical methods for modifying vascular valves. The surgical methods include the modification of valve leaflets with a remodelable material.

Advantageous such remodelable materials include extracellular matrix (ECM) material, such as mammalian small intestine submucosa.

In another aspect, the invention provides a method for modifying a vascular valve in a patient that includes connecting at least two valve leaflets of a vascular valve in at least one location with a remodelable material, so as to promote tissue of the patient to remodel and connect or fuse the leaflets. In certain aspects, the remodelable material can include an extracellular matrix material, such as mammalian porcine submucosa.

In another aspect, the invention provides a method for modulating the flow of blood in a vascular vessel that includes connecting together a region of at least two valve leaflets in a vascular valve with an extracellular matrix material. In certain aspects, the extracellular matrix material can comprise one or more sutures.

In yet another aspect, the invention provides a valve modification method that includes clipping venous valve leaflets together with a clip comprising a remodelable material in a manner such that the clip encourages remodeling, thereby causing the valve leaflets to fuse with patient tissue.

In yet another aspect, the invention provides a method for treating a venous insufficiency in a leg of a patient that includes connecting a first valve leaflet in a venous valve to a second valve leaflet in the venous valve with at least one bioremodelable material, so as to promote tissue of the patient to remodel the bioremodelable material to connect the first valve leaflet to the second valve leaflet. In certain aspects, the bioremodelable material is a clip for connecting the valve leaflets.

In another aspect, the invention provides a valve modification method involving positioning a remodelable material between two venous valve leaflets, followed by inserting a connector such as a staple through the leaflets and the remodelable material, such that the remodelable material causes the valve leaflets to fuse with patient tissue.

In yet other aspects, the invention provides systems for percutaneously modifying a valve or valves in a vascular vessel with a remodelable material.

The present invention provides improved and/or alternative methods and systems for modifying vascular valves. Additional embodiments and features and advantages of the invention will be apparent from the descriptions herein.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, the present invention provides methods that include modifying a vascular valve by attachment of a remodelable material to the valve, such that the remodelable material promotes in-growth of patient tissue into the remodelable material and modifies the function of the valve. The invention also provides methods of delivering remodelable and/or bioabsorbable material to vascular valves, as well as methods of securing remodelable material to vascular valve leaflets.

Turning now to a discussion of venous valves, depending on the stage and severity of venous valve insufficiency, several modes of venous valve failure can exist in one or more valves in one or more vein. For example, in a distended vein, the leaflets may allow undesirable or deleterious retrograde flow because the leaflet cusps no longer proximately locate one another when the valve is in its closed position. Alternatively, one or more valve leaflets may tear, causing only a portion of a leaflet cusp or leaflet to allow undesirable retrograde flow. Still alternatively, one or more leaflets may degenerate to the point that the leaflets or a portion of the leaflets fail to proximately locate in order to prevent deleterious back flow.

Figure 1:
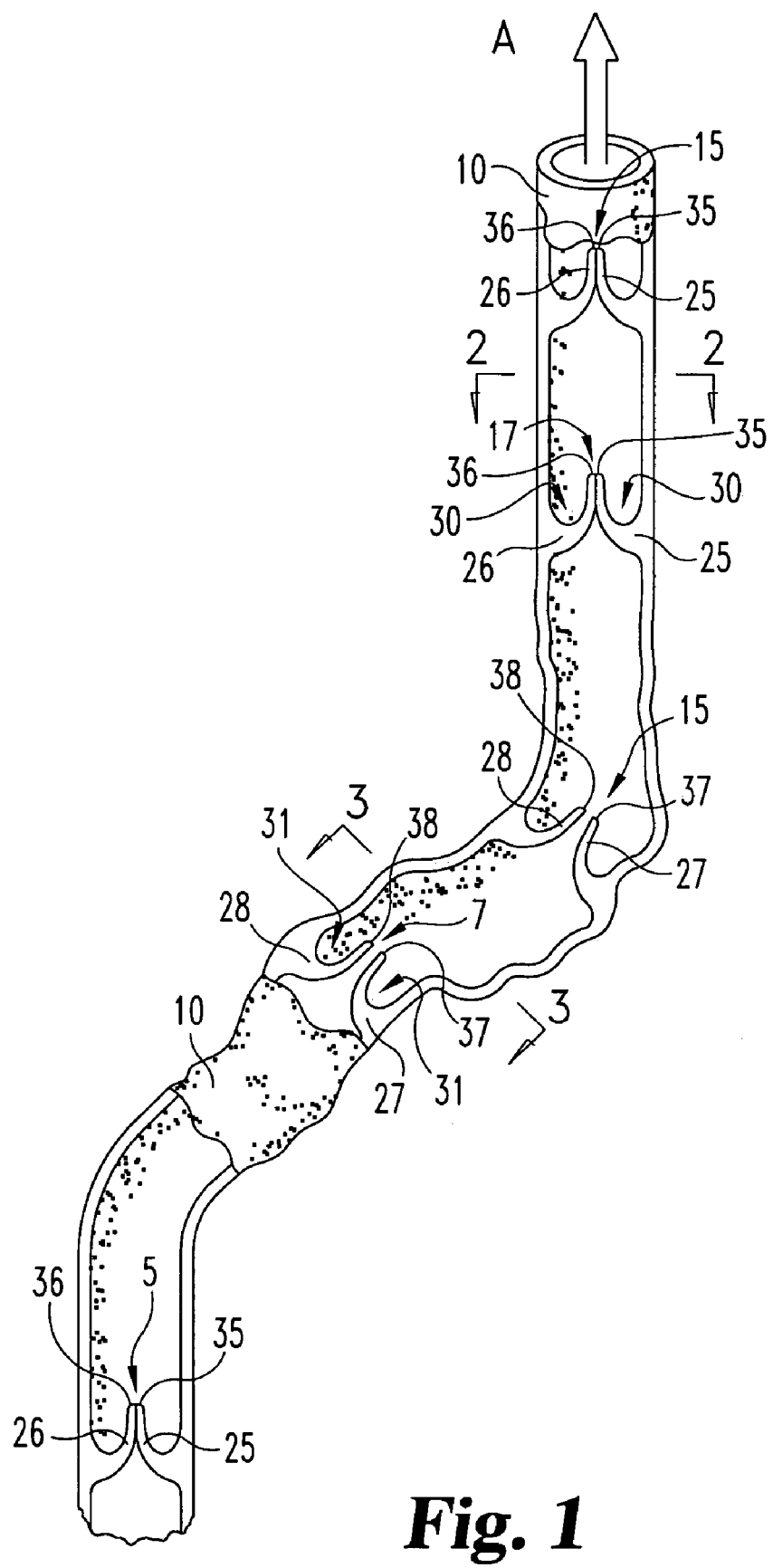
FIG. 1 is a perspective view, in partial cross-section, showing a vascular vessel having both adequate and inadequate valves.
Figure 2:
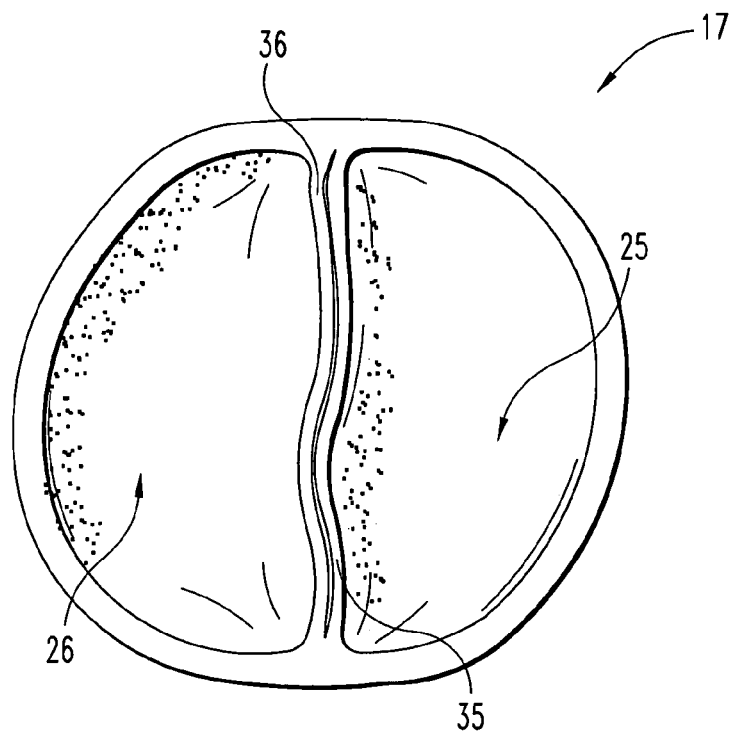
FIG. 2 is a perspective view taken along line 2-2 in FIG. 1 showing an adequate bicuspid vascular valve.

As shown in FIG. 1, more than one venous valve may become inadequate in the same vein. FIG. 1 depicts a portion of a vein 10 containing two inadequate venous valves 7, 15 and three adequate venous valves 5, 15, 17. The venous valves in FIG. 1 are bicuspid valves, each having two valve leaflets, exemplified in valve 5 by numerals 25 and 26. In an adequate venous valve 17, each leaflet 25, 26 extends into the vein 10 lumen and projects downstream A toward the heart. In so doing, each leaflet defines a reservoir 30, which collects blood during retrograde flow forcing each valve leaflet 25, 26 to close. FIG. 2, a cross sectional view taken along line 2-2 in FIG. 1, depicts an adequate venous valve 17 in its closed position. As shown, the lip 35, 36 of each leaflet is located proximate one another in order to prevent undesirable retrograde blood flow.

Figure 3:
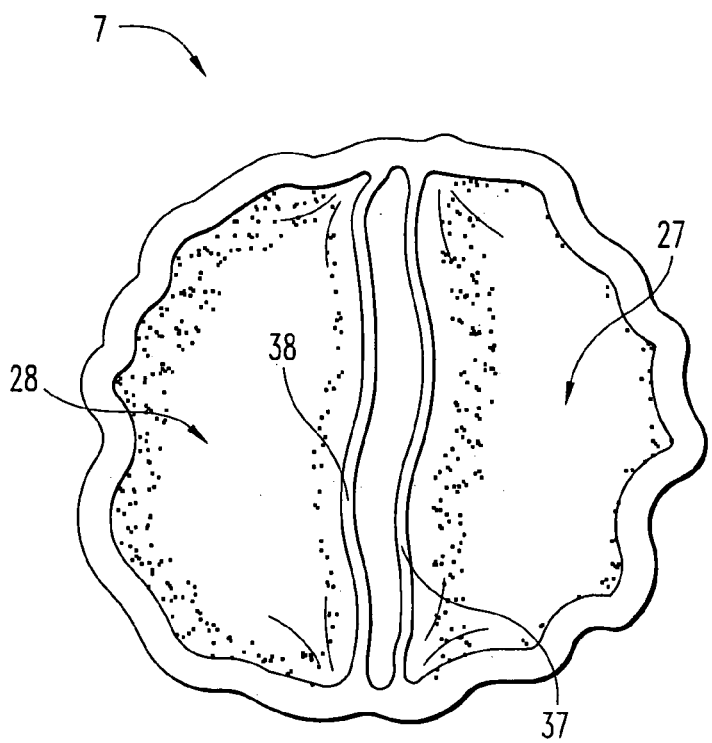
FIG. 3 is a perspective view taken along line 3-3 in FIG. 1 showing an inadequate bicuspid vascular valve.
Figure 4:
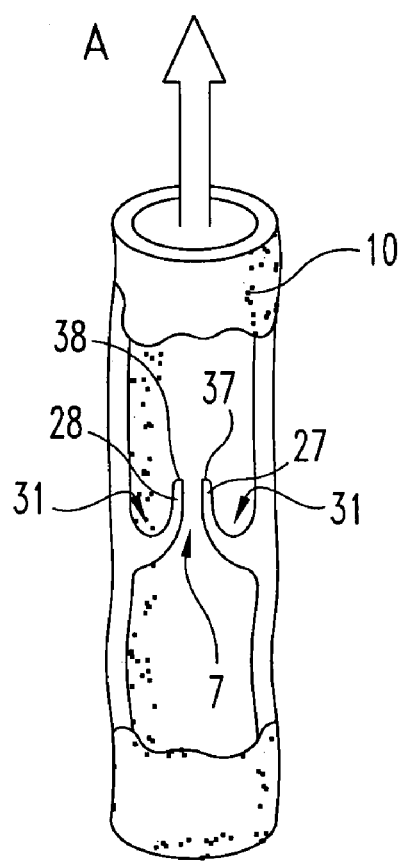
FIG. 4 is a perspective view, in partial cross-section, showing an inadequate bicuspid vascular valve.

For a number of reasons, as discussed above, the valve leaflets 27, 28 in an inadequate valve 7 may fail to prevent deleterious retrograde blood flow. When this occurs, at least a portion of the leaflet cusps 37, 38 fail to sufficiently locate proximate one another to prevent the undesirable back flow of blood. One mode of valve failure is displayed in FIG. 4, which shows a cross-section of inadequate valve 7 taken along the valve's vertical centerline. In FIG. 4, it is apparent that the valve cusps or lips 37, 38 do not sufficiently locate at the center or other points along each valve leaflet 27, 28 to adequately prevent undesirable retrograde blood flow. Another mode of valve failure is displayed in FIG. 3, which depicts a horizontal cross-section taken along line 3-3 in FIG. 1. In FIG. 3, it is apparent that valve cusps 37, 38 do not sufficiently locate across substantially the entire lumen of vessel 10 to adequately prevent deleterious retrograde blood flow. Alternatively, the cusps in an inadequate valve may fail to sufficiently locate at any one or more locations across the vessel lumen to adequately prevent undesirable retrograde blood flow, or a tear or aperture may be present in at least one of the valve leaflets 27, 28 thereby allowing deleterious retrograde flow to occur.

In certain embodiments, a surgical method can include connecting valve leaflets 37, 38 in an inadequate valve 7 with a remodelable material in order to reduce the quantity of retrograde blood flow through that valve. As discussed below, the remodelable material will promote remodeling such that the patient's tissue grows within or into the remodelable material.

Illustratively, a surgical method can include a venous catheterization. Access can be established at a location proximate the patient's ankle, or, alternatively, access may be obtained at any suitable location on the patient's body, such as the neck or knee. In alternative embodiments, access can be established surgically, by performing a cutdown, or other suitable surgical method, to the appropriate vein in any suitable location.

After access is achieved, a remodelable material can be delivered to an inadequate valve. Delivery of the remodelable material to the inadequate valve can be achieved in any suitable manner, a number of which are known in the art. One such delivery method involves delivery of the remodelable material with a catheter. For example, the material can be placed and held on the distal tip of a gripper, operated by either suction or mechanical means, e.g. claws, and then delivered to the inadequate valve by pushing the gripper and material through the catheter to the valve. For additional information concerning percutaneous delivery and positioning of material, reference can be made, for example, to U.S. Pat./application Nos. 5,609,598, 5,810,847, 6,149,660, 6,575,971, 6,695,866, 2003/0093071, and/or 2004/0167539.

After delivery to the target site, the remodelable material can be secured to pertinent valve leaflets with a suitable securing device and/or method. For example, the material can be secured using one or more sutures, staples, and/or temporary or permanent clamps, clips, or barbs. If a temporary securing method is used, the device can optionally be percutaneously or surgically retrieved at a later time, or optionally, the device can be made of a bioremodelable and/or bioabsorbable material, such that retrieval is not necessary for removal of the device. In additional embodiments, the remodelable material can be fashioned into a clip, clamp, and/or barb, which is then used to connect or bring together the valve leaflets and promote fusion of the valve leaflets with patient tissue. As such, delivery and placement of the clamp, clip, and/or barb can occur using an instrument, such as a catheter, which can optionally contain multiple clamps, clips, and/or barbs for deployment within the vasculature. Still alternatively, a remodelable material may be incorporated in a gel or glue that is contacted with the valve leaflets which are brought into contact with and held against each other, e.g. with a suture, clip or clamp and/or by the bonding function of the gel or glue. Yet still alternatively, in additional embodiments, the remodelable material can comprise a three-dimensional shape that is placed between the leaflets and is secured using a staple or suture, for example a suture made from an ECM material.

Multiple techniques are known in the art to suture, staple, and/or clip or fasten tissue percutaneously. For example, a catheter including a gripper with a mechanical claw can be used to place a clip or barb onto or through valve leaflets. Alternatively, a mechanized suturing device can be inserted through a catheter and delivered to the valve leaflets in order to suture material to each leaflet, or alternatively, suture the leaflets together. Still alternatively, a stapling device can be attached to the end of a catheter and positioned adjacent to the valve leaflets in order to secure material to those leaflets. For additional information as to clipping, suturing, and/or stapling techniques useful in the present invention, reference can be made, for example, to U.S. Pat. Nos. 5,609,598, 5,584,861, 5,810,847, 6,149,660, 6,695,866, 6,575,971, and/or European Patent Application EP 442,588, and/or Great Britain Patent Application GB2,165,559. Still further, energy-driven tissue welding or bonding techniques can be used in combination with solid or flowable ECM materials to attach one or more portions of the leaflets together such that remodeling promoted by the ECM material fuses the leaflets together. For example, an amount of ECM material can be positioned between leaflet portions in location(s) where patient-tissue-fusion is desired, and two or more energy-delivering (e.g., RF delivering) probes can be used to force the leaflets against the inner piece or amount of ECM material. The probes can then be used to deliver energy and fuse or bond each leaflet to a respective side or location of the ECM material. Afterward, the ECM material will promote remodeled fusion of the targeted leaflet location(s).

Valve modification can be performed on any one or more vascular valve in any one or more vein or artery as is suitable. In a vein with more than one inadequate valve, the valve located furthest from access can be the first valve modified. In FIG. 1, for example, in certain embodiments, access can be obtained upstream of both inadequate valves 7, 15. In these embodiments, the inadequate venous valve 15 located furthest downstream can be modified before the more upstream inadequate venous valve 7. In alternative embodiments, access can be obtained downstream of both inadequate valves 7, 15. In these embodiments, the inadequate valve 7 located furthest upstream can be modified before the more downstream valve 15. Alternatively, in other embodiments, inadequate venous valves in a common vein can be modified in any suitable order.

When modifying multiple valves in a common vessel, the remodelable or bioabsorbable material, whether it be in the form of a device, such as a clip, layer, and/or gel, can be delivered on an as needed basis or, alternatively, multiple materials can be stored in the delivery device. For example, in embodiments where material is delivered on an as-needed basis, the delivery device, i.e. gripper, can be removed from the catheter after material delivery, reloaded with new material, and then re-inserted into the catheter as more material is needed. Alternatively, if a delivery device or catheter containing multiple materials is used, the device does not need to be removed from the vasculature in between valve modifications.

Figure 5:
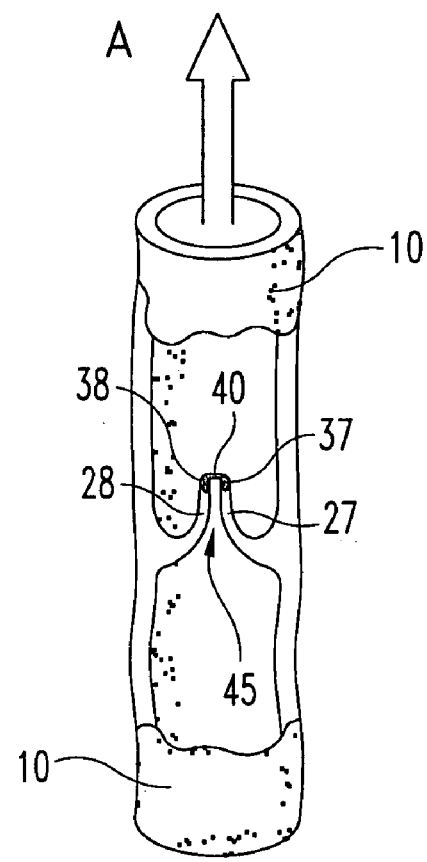
FIG. 5 is a perspective view, in partial cross-section, showing a bicuspid vascular valve that has been modified with a remodelable and/or bioabsorbable material.
Figure 6:
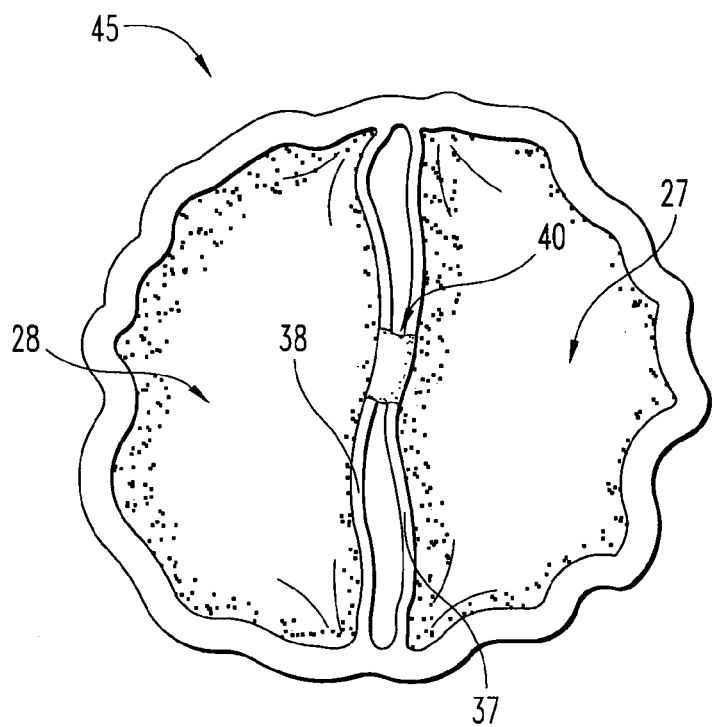
FIG. 6 is a perspective cross-sectional view of a vascular vessel showing a bicuspid valve modified in one location with a remodelable and/or bioabsorbable material.

With reference now to FIGS. 5 and 6, illustratively, a venous valve can be modified by securing a remodelable and/or bioabsorbable material 40 to the leaflets 27, 28 of an inadequate venous valve 45. As depicted in FIG. 6, the material 40 can be first secured to valve leaflet 27, and or lip 37, and then secured to leaflet 28, and or cusp 38, in a manner such that the open space between leaflets 27 and 28 is reduced. The material 40 can be secured to the leaflets 27, 28 using any suitable securing method discussed above, such as sutures, staples, clips, and/or bonding agents. In certain embodiments, sutures made from a remodelable material, such as an ECM material, discussed in more detail below, can be used. In alternative embodiments, a material and both leaflets can be simultaneously secured together with one or more suture, staple, and/or clip, such as a bioabsorbable staple or clip. For example, a material, in solid or gel form, can be placed in between the leaflets and secured for instance by inserting a connector such as a staple, barb, and/or suture through both leaflets and the material or holding the leaflets together by a device such as a clip or clamp. In still alternative embodiments, the leaflets can be modified by suturing portions or regions of them together with a remodelable suture, such as a suture made from an ECM material, such as small intestine submucosa.

Figure 7:
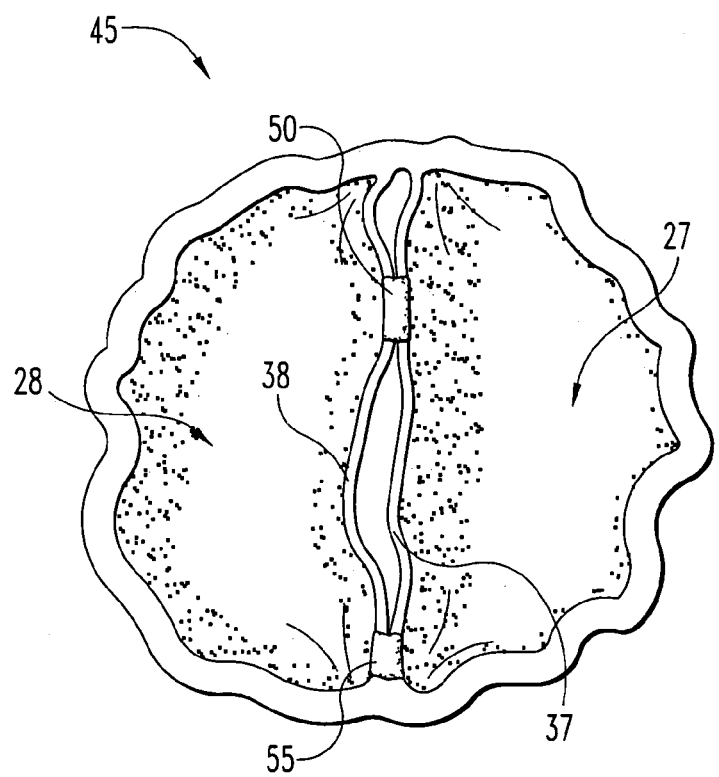
FIG. 7 is a perspective cross-sectional view of a vascular vessel showing a bicuspid valve modified in two locations with remodelable and/or bioabsorbable materials.

As is illustratively shown in FIG. 6, the remodelable and/or bioabsorbable material 40 can be placed approximately along the central axis of the venous lumen. However, in other embodiments, the material can be placed in any suitable location or locations along the valve leaflets. For example, FIG. 7 depicts an embodiment where two materials 50, 55 are used to modify a venous valve. Either one or both materials 50, 55 can be a remodelable material or a bioabsorbable material or any suitable combination thereof.

Figure 8:
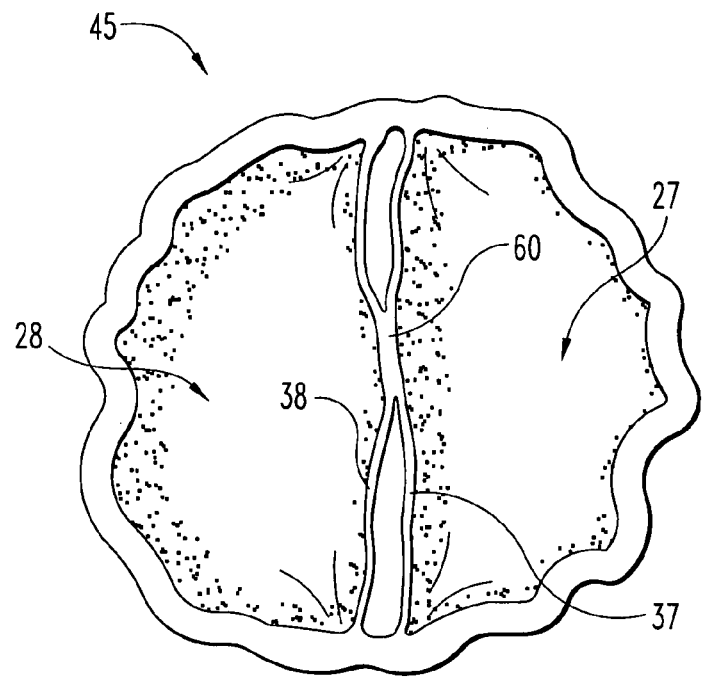
FIG. 8 is a perspective cross-sectional view of a vascular vessel showing a remodeled bicuspid vascular valve of the present invention.

Turning now to FIG. 8, the modified valve of FIG. 6 is shown after a period of time sufficient to allow the patient's tissue to remodel the remodelable and/or bioabsorbable material 40. As shown in FIG. 8, the remodelable material 40 has been replaced with the patient's native tissue 60 in such a manner as to sufficiently maintain the valve leaflets 27, 28 and cusps 37, 38 in their modified position.

Figure 9:
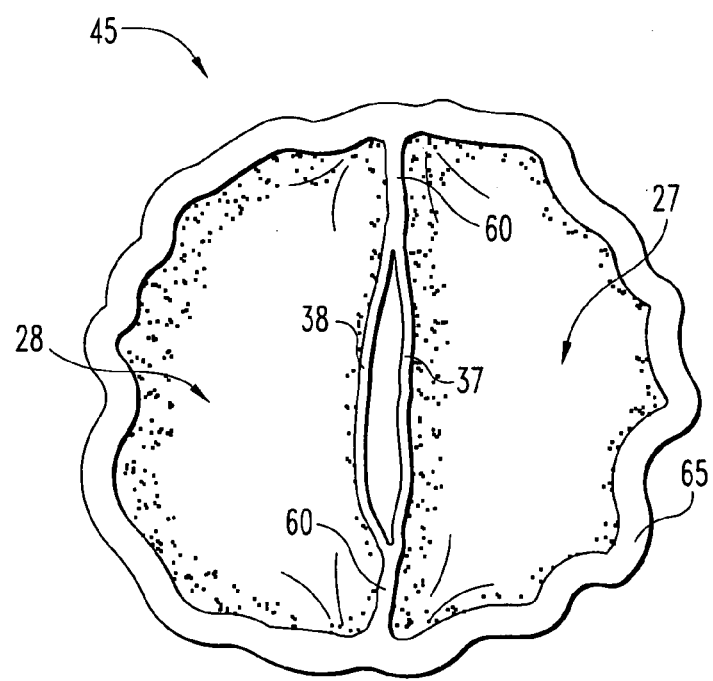
FIG. 9 is a perspective cross-sectional view of a vascular vessel showing a remodeled bicuspid vascular valve of the present invention.

Additionally, as shown in FIG. 9, the valve leaflets 27, 28 can be modified in a location approximate the junction of each valve leaflet 27, 28 with the vessel wall 65. The valve in FIG. 9 is shown in its remodeled state, such that the patient's native tissue 60 is maintaining the valve 45 in its modified form.

Valve modification can include the use of one or more remodelable materials, of any suitable shape, size, and/or construction, in any suitable location or locations along the valve leaflets and/or vessel wall. For example, in certain embodiments, the remodelable material may be placed between portions of two or more valve leaflets and secured in place using suitable glue or bonding agents. Alternatively, the remodelable material may be secured to the upstream side of each valve leaflet, or the upstream side of one or more leaflets and the downstream side of other leaflet(s), as is necessary. Still alternatively, the remodelable material may be secured to the valve leaflets using electrodes equipped with an energy source, such as radiofrequency (RF) energy. The surgical methods of this invention can be used to modify any vascular valve, arterial or venous, monocuspid, bicuspid, tricuspid, or otherwise.

The remodelable materials of the invention can include collagenous extracellular matrix (ECM) materials, such as submucosa, renal capsule membrane, dura mater, pericardium, serosa, peritoneum, or basement membrane. The preferred medical graft products of the invention will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa, more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

As prepared, the extracellular matrix material may optionally retain growth factors or other bioactive components native to the source tissue. For example, the matrix material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material of the invention may include other biological materials such as heparin, heparin sulfate, hyaluronic acid, fibronectin and the like. Thus, generally speaking, the ECM material may include a bioactive component that induces, directly or indirectly, a cellular response such as a change in cell morphology, proliferation, growth, protein or gene expression. Further, in addition or as an alternative to the inclusion of such native bioactive components, non-native bioactive components such as those synthetically produced by recombinant technology or other methods, may be incorporated into the ECM material.

ECM material used in the invention is preferably highly purified, for example, as described in U.S. Pat. No. 6,206,931. Thus, preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 $\mu$ g/mg, more preferably less than about 2 $\mu$ g/mg, and virus levels are preferably less than about 50 plate forming units (PFU) per gram, more preferably less than about 5 PFU per gram. The ECM material used in the invention is preferably disinfected with an oxidizing agent, particularly a peracid, such as peracetic acid. These and additional properties of submucosa taught in U.S. Pat. No. 6,206,931 may be characteristic of the ECM material used in the present invention.

The remodelable ECM or other material may include one or more radiopaque markers or a radiopaque coating or impregnation to assist in visualization of the material during a non-invasive procedure. For example, radiopaque substances containing tantalum, barium, iodine, or bismuth, e.g. in powder form, can be coated upon or incorporated within the ECM or other remodelable material.

The remodelable material of the invention may also include a synthetic material, such as a bioabsorbable synthetic polymer, such as polylactic acid or polycaprolactone, for example. The remodelable material may also be a combination, or hybrid, of ECM material and synthetic material. For further information concerning suitable bioabsorbable synthetic materials useful in certain embodiments of the invention, reference can be made, for example, to U.S. Utility Patent Application titled, "Implantable Frame with Variable Compliance, " filed on Apr. 11, 2005 ("Express Mail" Mailing Label No. EV 327 135 804 US).

It is also possible for an ECM-based remodelable material used in the invention to comprise a multilaminate ECM material. To form a multilaminate material, two or more ECM segments are stacked, or one ECM segment is folded over itself at least one time, and then the layers are fused or bonded together using a bonding technique, such as chemical cross-linking or vacuum pressing during dehydrating conditions.

In accordance with aspects of the invention, an adhesive, glue or other bonding agent may be used in achieving a bond between ECM layers, and/or ECM material and a valve leaflet and/or patient tissue, such as a vessel wall. Suitable bonding agents may include, for example, collagen gels or pastes, gelatin, or other agents including reactive monomers or polymers, for example cyanoacrylate adhesives. As well, bonding can be achieved or facilitated using chemical cross-linking agents, such as glutaraldehyde, formaldehyde, epoxides, genipin or derivatives thereof, carbodiimide compounds, polyepoxide compounds, or other similar agents. Cross-linking of ECM materials can also be catalyzed by exposing the matrix to UV radiation, by treating the collagen-based matrix with enzymes such as transglutaminase and lysyl oxidase, and by photocross-linking. The combination of one or more of these with dehydration-induced bonding may also be used.

In accordance with another aspect of the invention, different drying or dehydration methods can be used to fuse ECM portions of the bioremodelable material. In one preferred embodiment, the multiple layers of ECM material are compressed under dehydrating conditions. The term "dehydrating conditions" is defined to include any mechanical or environmental condition which promotes or induces the removal of water from the ECM material. To promote dehydration of the compressed ECM material, at leeast one of the two surfaces compressing the matrix structure can be water permeable. Dehydration of the ECM material can optionally be further enhanced by applying blotting material, heating the matrix structure or blowing air, or other inert gas, across the exterior of the compressing surfaces. One particularly useful method of dehydration bonding ECM materials is lyophilization, e.g. freeze-drying or evaporative cooling conditions.

Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

In yet still further applications, a remodelable gel can be formed from fluidized compositions, as illustrated in U.S. Pat. Nos. 5,275,826, 5,516,533, 6,206,931, 6,444,229 and/or in International Publication No. WO2005020847 (Cook Biotech Incorporated) published Mar. 10, 2005, which are each hereby incorporated by reference in their entirety. In this regard, solutions or suspensions of ECM can be prepared by comminuting and/or digesting ECM with a protease (e.g. trypsin or pepsin), for a period of time sufficient to solubilize the ECM and form substantially a homogenous solution. The ECM starting material is desirably comminuted by tearing, cutting, grinding, shearing or the like. Grinding the ECM in a frozen or freeze-dried state is advantageous, although good results can be obtained as well by subjecting a suspension of pieces of the submucosa to treatment in a high speed blender and dewatering, if necessary, by centrifuging and decanting excess waste. The comminuted ECM can be dried, for example freeze dried, to form a powder. Thereafter, if desired, the powder can be hydrated, that is, combined with water or buffered saline and optionally other pharmaceutically acceptable excipients, to form a fluid medical graft composition, e.g. having a viscosity of about 2 to about 300,000 cps at 25° C. The higher viscosity graft compositions can have a gel or paste consistency. This gelatinous medical graft composition can be placed between valve leaflets before securing the leaflets together in order to induce the leaflets to grow together.

Additionally, such gelatinous or flowable materials can include solubilized and/or particulate ECM components, and in preferred forms include ECM gels having suspended therein ECM particles, for example having an average particle size of about 50 microns to about 500 microns, more preferably about 100 microns to about 400 microns. The ECM particulate can be added in any suitable amount relative to the solubilized ECM components, with preferred ECM particulate to ECM solubilized component weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth. Flowable ECM materials can also be used in conjunction with other occlusive devices as described herein, or otherwise.

The invention also encompasses medical products or kits, such as a prosthesis device of the invention configured to connect two or more valve leaflets, or a catheter loaded with at least one such prosthesis device sealed within sterile medical packaging. The final, packaged product is provided in a sterile condition. This may be achieved, for example, by gamma, e-beam or other irradiation techniques, ethylene oxide gas, or any other suitable sterilization technique, and the materials and other properties of the medical packaging will be selected accordingly. The prosthesis device may be packaged wet or after it is dried.

Surgical methods in accordance with the present invention can be used to modify vascular valves in mammalian patients, including humans. Preferred surgical methods of the invention find particular utility in repairing venous valves, such as in deep veins or superficial veins. For example, surgical methods of the invention are used with preference in the treatment of venous valve insufficiency.

All publications cited herein are hereby incorporated herein by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for modifying a vascular valve in a patient, comprising:
   connecting at least two valve leaflets in a vascular valve in at least one location with an extracellular matrix material, so as to promote tissue of the patient to remodel and connect said leaflets, wherein said extracellular matrix material is in the form of a suture.

2. The method of claim 1, wherein said extracellular matrix material comprises, submucosa, dura mater, pericardium, renal capsule membrane, or basement membrane.

3. The method of claim 2, wherein said submucosa comprises mammalian submucosa.

4. The method of claim 3, wherein said mammalian submucosa comprises porcine, bovine, or ovine submucosa.

5. The method of claim 4, wherein said porcine submucosa comprises adult porcine submucosa.

6. The method of claim 3, wherein said mammalian submucosa comprises intestinal submucosa, stomach submucosa, urinary bladder submucosa, or uterine submucosa.

7. The method of claim 1, wherein said remodelable material comprises a bioabsorbable synthetic polymer.

8. A method for modifying a vascular valve in a patient, comprising:
   connecting at least two valve leaflets in a vascular valve in at least one location with a remodelable material, so as to promote tissue of the patient to remodel and connect said leaflets, wherein said remodelable material is a hybrid of extracellular matrix material and bioabsorbable synthetic polymer.

9. A method for modulating the flow of blood in a vascular vessel, comprising:
   connecting together at least two valve leaflets in a vascular valve with an extracellular matrix material, wherein said extracellular matrix material is connected to the center of each valve leaflet at least in part by a suture.

10. The method of claim 9, wherein said vascular valve is a venous valve.

11. The method of claim 10, wherein said vascular valve has two valve leaflets.

12. The method of claim 11, wherein said valve leaflets are connected in at least one location proximate the junction of each valve leaflet to the common wall of said vessel.

13. A method for modulating the flow of blood in a vascular vessel, comprising:
   connecting together at least two valve leaflets in a vascular valve at the center of each leaflet with an extracellular matrix material, wherein said extracellular matrix is a multilaminate sheet of extracellular matrix material.

14. A method for modulating the flow of blood in a vascular vessel, comprising:
   connecting together at least two valve leaflets in a vascular valve at the center of each leaflet with an extracellular matrix material, wherein said extracellular matrix material comprises a twisted band of mammalian submucosa.

15. A method for modulating the flow of blood in a vascular vessel, comprising:
   connecting together at least two valve leaflets in a vascular valve at the center of each leaflet with an extracellular matrix material, wherein said extracellular matrix material comprises a gel.

16. A method for treating a venous insufficiency in a leg of a patient, comprising:
   connecting a first valve leaflet in a venous valve to a second valve leaflet in the venous valve with at least one bioremodelable material comprising a gel form extracellular matrix material, wherein said bioremodelable material is placed between said first valve leaflet and said second valve leaflet and is secured with one or more staple, suture, and/or clip, so as to promote tissue of the patient to remodel said bioremodelable material to connect said first valve leaflet to said second valve leaflet.

17. The method of claim 16, wherein said bioremodelable material is delivered to said venous valve with a delivery device.

18. The method of claim 17, wherein said delivery device comprises a catheter.

19. The method of claim 16, wherein said securing comprises stapling.

20. The method of claim 16, wherein said bioremodelable material is small intestine submucosa and said clip comprises an ECM material.

21. The method of claim 16, wherein:
   said bioremodelable material is delivered to said venous valve with a delivery device,
   said bioremodelable material is positioned with a positioning device at a first location on said first valve leaflet and at a second location on said second valve leaflet; and
   said bioremodelable material is secured to said first valve leaflet at said first location and to said second valve leaflet at said second location.

22. The method of claim 21, wherein said positioning device is a catheter.

23. The method of claim 21, wherein said bioremodelable material is secured at least in part with staples.

24. A method for modulating the flow of blood in a vascular vessel, comprising:
   connecting together a region of at least two valve leaflets in a vascular valve with an extracellular matrix material, wherein said valve leaflets are connected in at least one location proximate the junction of each valve leaflet to the common wall of said vessel and wherein said extracellular matrix is a multilaminate sheet of extracellular matrix material.

25. A method for modulating the flow of blood in a vascular vessel, comprising:
   connecting together a region of at least two valve leaflets in a vascular valve with an extracellular matrix material, wherein said valve leaflets are connected in at least one location proximate the junction of each valve leaflet to the common wall of said vessel and wherein said extracellular matrix material comprises a twisted band of mammalian submucosa.

26. A method for modulating the flow of blood in a vascular vessel, comprising:
   connecting together a region of at least two valve leaflets in a vascular valve with an extracellular matrix material, wherein said valve leaflets are connected in at least one location proximate the junction of each valve leaflet to the common wall of said vessel and wherein said extracellular matrix material comprises a gel.

* * * * *